United States Patent [19]

Dauphinee et al.

[11] Patent Number: 4,511,845
[45] Date of Patent: Apr. 16, 1985

[54] SALINOMETER

[75] Inventors: Thomas M. Dauphinee; Christopher G. M. Kirby, both of Ottawa, Canada

[73] Assignee: Canadian Patents & Development Limited, Ottawa, Canada

[21] Appl. No.: 416,013

[22] Filed: Sep. 8, 1982

[51] Int. Cl.³ .............................. G01N 27/02
[52] U.S. Cl. ..................... 324/444; 324/441; 324/450; 204/242; 204/244; 204/406; 204/411
[58] Field of Search ............... 324/441, 444, 450, 446, 324/449; 73/170 R, 170 A; 204/242, 244, 274, 408, 409, 411, 406

[56] References Cited

U.S. PATENT DOCUMENTS 2,769,140 10/1956 Obenshain ........................ 324/450
3,963,979 6/1976 Dauphinee ....................... 324/444
3,993,945 11/1976 Warmoth et al. ................ 324/449

Primary Examiner—Michael J. Tokar
Assistant Examiner—Kevin D. O'Shea
Attorney, Agent, or Firm—Edward Rymek

[57] ABSTRACT

The salinometer is based on a direct determination of the conductivity ratio $R_t = (C_x/C_s)_t$ of sample water to standard seawater in a two channel, dual-cell, continuous-flow system. Each of the channels includes a conductivity cell with four electrodes immersed in sequence in the water flow. Two of the electrodes are current electrodes and the other two electrodes are potential electrodes. The standard water and the sample water pumped into their respective channels, are maintained at a common temperature by heat exchangers and a common bath. The salinometer circuitry include a first current source for driving a controlled current into the current electrodes of the conductivity cell to maintain a constant voltage across the potential electrodes. A second current source drives a current which is a linear function of the first controlled current into the current electrodes of the conductivity cell in the reference channel. The conductivity ratio $R_t$ is then a function of the voltage detected between the voltage electrodes in the reference source.

8 Claims, 3 Drawing Figures

000
SALINOMETER

BACKGROUND OF THE INVENTION

This invention is directed to apparatus for the measurement of conductivity of a liquid and in particular, to a salinometer for the measurement of the ratio of the conductivity of saltwater to that of standard seawater.

In U.S. Pat. No. 3,963,979, which issued on June 15, 1976, to T. M. Dauphinee, a laboratory salinometer is described. It is based on continuous flow of sample water at a constant temperature, ensured by a heat exchanger and thermostatted bath, through the measuring cell, rather than measurements on discrete samples as was the case with prior systems. The advantages of the system were that complicated temperature compensations in the measuring circuit were eliminated while the continuous flow greatly simplified flushing of the system to remove all traces of the previous sample. This instrument in its commercial version, the Guildline Autosal, has now become the standard instrument in many oceanographic laboratories around the world.

A sophisticated version of the same system, using two heat exchanger-cell units in two different thermostatted baths, was developed for studies of the conductivity of seawater as a function of salinity and temperature, and of the KCl equivalent of standard seawater. The results obtained led to the form of equations used for the Practical Salinity Scale, 1978, which is described in the publication by E. L. Lewis, "The Practical Salinity Scale 1978 and its Antecedents", IEEE Journal of Oceanic Engineering, Vol. OE-5, pp 3–8, January 1980, and make up a substantial part of the data on which the new scale is based.

The bulk and weight of the Autosal, which resulted largely from the thermosetting system, made it unsuitable for use in any but a fixed location or the laboratory of a relatively large ship. However, a need is apparent for an instrument that is suitable for field and small boat use, can be easily transported from place to place, requires much less sample than the 100–200 ml needed by the Autosal and other salinometers, but is still accurate enough to satisfy most oceanographers' needs.

SUMMARY OF THE INVENTION

It is therefore an object of this invention to provide an accurate and portable salinometer for field use.

This and other objects are achieved in a salinometer that includes two channels, a reference water channel and a sample water channel. In each of the channels, the predetermined water is fed into the channel from a source. A conductivity cell in each channel has four electrodes immersed in sequence in the water flow, two of the electrodes being current electrodes and the other two electrodes being potential electrodes. Further, the channels include a mechanism to assure that the water temperatures in the two cells are substantially the same. The conductivity ratio $R_t$ between the sample water and the reference water is determined as a function of the voltage $V_s$ between the reference cell voltage electrodes and the voltage $V_x$ between the sample cell voltage electrodes when linearly identical currents are driven between the current electrodes in each of the conductivity cells.

In accordance with another aspect of this invention, the common temperatures of the water in the two channels is maintained by a heat exchanger which is located in each channel, and through which water flows to the conductivity cell. The heat exchangers which may be made of metal tubing and may be in thermal and/or electrical contact with one another while immersed in a liquid bath.

The circuit for driving the conductivity cells includes a first current source for driving a first controlled current between the two current electrodes in the sample cell, which may be the second and fourth electrodes, to produce a constant voltage between the two potential electrodes, which may be the first and third electrodes. A second current source drives a second controlled current between the two current electrodes in the reference cell, these electrodes may be the second and fourth electrodes. The second controlled current is controlled to be a linear function of the first controlled current. A detector senses the voltage between the potential electrodes in the reference cell, these electrodes may be the first and third electrodes. In addition, the first electrodes in the cells may be maintained at a common potential preferably that of the heat exchangers to avoid the creation of stray currents between the channels through the heat exchangers.

Many other objects and aspects of the invention will be clear from the detailed description of the drawings.

DETAILED DESCRIPTION

Figure 1:
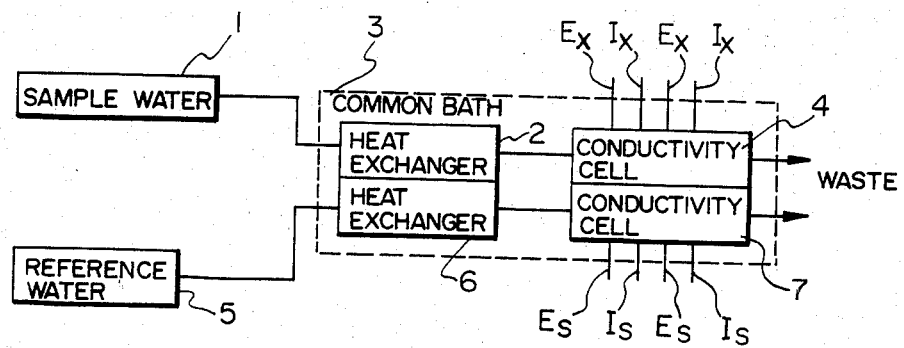
FIG. 1 is a block diagram of the two channel salinometer.

A schematic of the salinometer in accordance with the present invention is illustrated in FIG. 1. The flow system consists of two separate but near-identical channels, one channel for sample water and the other channel for reference water. In one channel, sample water is pumped from a reservoir 1 to a heat exchanger 2 located in a water bath 3 which is stirred. From the heat exchanger 2, the sample water flows through a conductivity cell 4 which has two current electrodes $I_{1x}$ and $I_{2x}$ and two potential electrodes $E_{1x}$ and $E_{2x}$ which are coupled to a measuring circuit. From cell 4, the sample water flows out as waste.

In the second channel, reference water is pumped from a reservoir 5 through a second heat exchanger 6 also located in the water bath 3, such that the temperature of the reference water is made substantially identical to the temperature of the sample water. The reference water then flows through the conductivity cell 7 which has two current electrodes $I_{1s}$ and $I_{2s}$ and two potential electrodes $E_{1s}$ and $E_{2s}$ which are also coupled to the measuring circuit. From cell 7, the reference water flows out as waste.

In this system, the necessity of either thermostatting or a complicated temperature compensation system is avoided by making a direct measurement of the conductivity ratio $R_t = C_x/C_s$ as it is used in the new scale, i.e.

$$S = \sum_{j=0}^{5} a_j + \frac{(t-15)}{1+k(t-15)} b_j R_t^{j/2} \tag{1}$$

where the $a_j$ are the constants $a_{,1}, a_{,2} \ldots a_{,5}$ defined in the scale t is celsius temperature k is 0.0162, and the $b_j$ are the constants $b_{,1}, b_{,2} \ldots b_{,5}$ defined in the scale By using this two heat exchanger-cell combination in the same stirred but not thermostatted bath, with small conductivity cells, the salinometer can be made portable.

Figure 2:
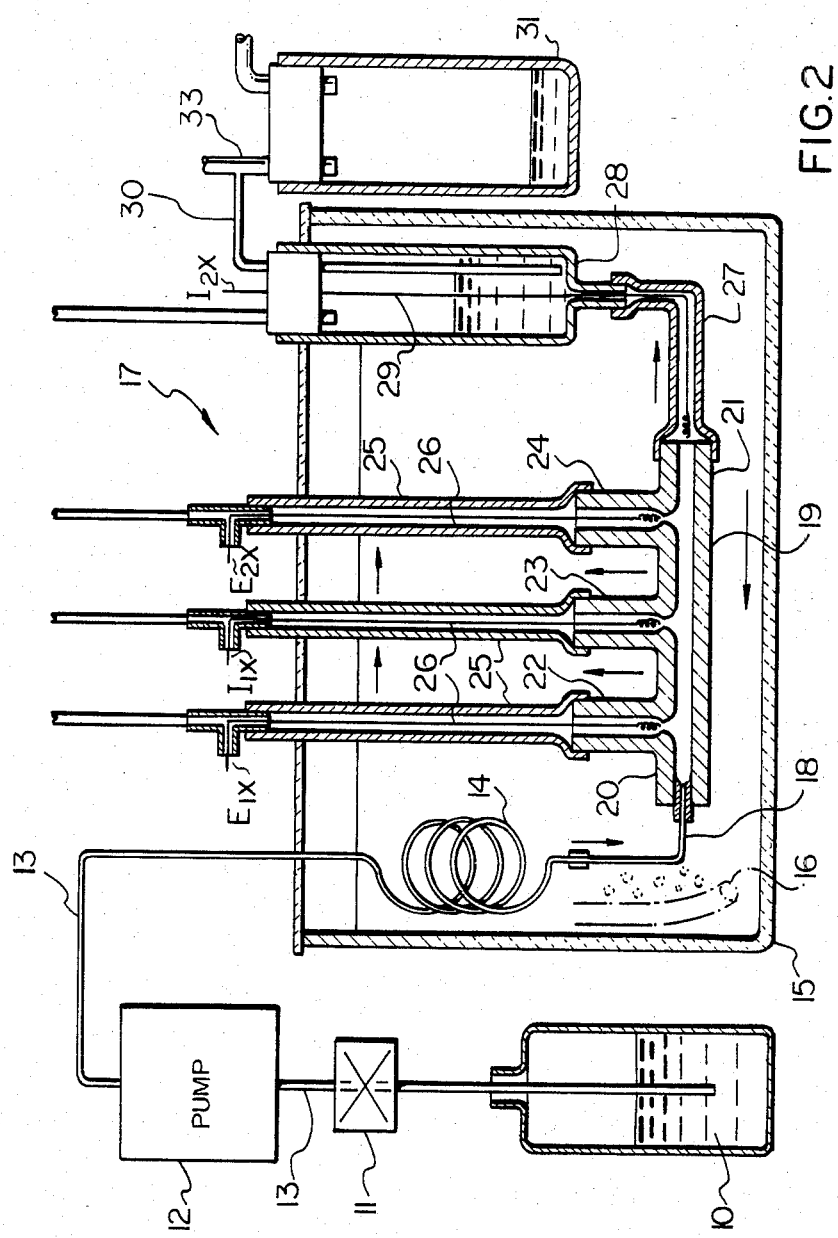
FIG. 2 is a cross-section of one channel in the salinometer.

One embodiment of one channel of the flow system apparatus is shown in cross-section in FIG. 2. The channel will be described as the sample channel, though both the sample and the reference channels are similar.

Sample water from a bottle 10 is drawn through a crosslink valve 11 by a peristaltic pump 12 through a thin Teflon [trademark] tube 13, and drives it through a heat exchanger tube 14 which is located in a clear glass dewar 15 filled with water. This water is stirred to ensure uniformity of temperature by a bubbler 16 fed by an aquarium-type pump (not shown). The heat exchanger tube 14 may be made of stainless steel having a length in the order of 30 cm and an I.D. of 1 mm. In order to assist in obtaining identical sample and reference water temperatures, the heat exchanger tube 14 may be soldered throughout its length to the heat exchanger tube in the other channel.

The tube 14 is connected to a conductivity cell 17 by a further Teflon tube 18. The cell 17 consists essentially of four electrodes $E_{1x}$, $I_{1x}$, $E_{2x}$ and $I_{2x}$ positioned sequentially along a flow path of the sample water. More specifically, the cell 17 includes a tube 19 having an inlet 20, an outlet 21 and three side arms 22, 23 and 24. The Teflon tube 18 is connected to the inlet 20. On each side arm 22, 23, 24, an open-ended tube 25 is mounted through which the leads 26 for the electrodes $E_{1x}$, $I_{1x}$ and $E_{2x}$, respectively pass, and by which atmospheric pressure is maintained on the liquid in the side arms. The fourth electrode $I_{2x}$ is mounted in the outlet 21. A tube 27 and an open ended reservoir 28 are connected to outlet 21 through which lead 29 for electrode $I_{2x}$ passes. As the water is pumped into the cell 17 by pump 12, it rises in each of the side arms 22, 23 and 24 at a very slow rate as the reservoir 28 fills. Since water continuously flows up arms 22, 23, 24 and out of outlet 21, the measuring zone in tube 19 remains uncontaminated during the measuring process.

After a measurement is taken, the water in the cell 17 and the reservoir 28 may be removed and the cell 17 may be flushed by a suction arrangement as shown in FIG. 2. This system includes a tube 30 which extends to the bottom of reservoir 28 and leads to a waste reservoir 31. If the storage reservoir 33 overflows, the water runs through the tube 30 to the waste reservoir 31. The waste reservoir 29 is pumped continuously by a pump (not shown) adapted from suction. A T-joint 33 is open to the air in the overflow line 30 from the reservoir 28. When it is blocked, the reservoir 28 first empties and then the water is pulled out of the cell 17 and its sidearms 22, 23, 24. These then refill through the action of the peristaltic pump 12.

Alternately, the water may be forced out of the arms in the cell 17 and the reservoir 28 by applying air pressure to the open ends of tubes 25 and reservoir 28 driving the water out. The next sample is then pumped into the cell 17 with a measurement being taken after the new sample is flushed through the cell 17 once or twice.

The standard or reference water channel is identical, except that an even smaller flow is used once the cell has been well flushed. It is normally flushed without completely emptying the sidearms, since the reference water is always the same, and this avoids delay in refilling.

In the present embodiment, it has been found that a sample flow as low as 3 ml/min and a reference flow as low as 1 ml/min gave very acceptable results.

In order to determine the conductivity of the sample water, identical currents are driven between the current electrodes $I_1$ and $I_2$ in each of the channels. The conductivity ratio $R_t$ then is effectively the ratio between the potentials across the potential electrodes in each of the channels, if we ignore the difference between the two cell constants caused by dimensional differences between the cells and also polarization at the potential electrodes.

Figure 3:
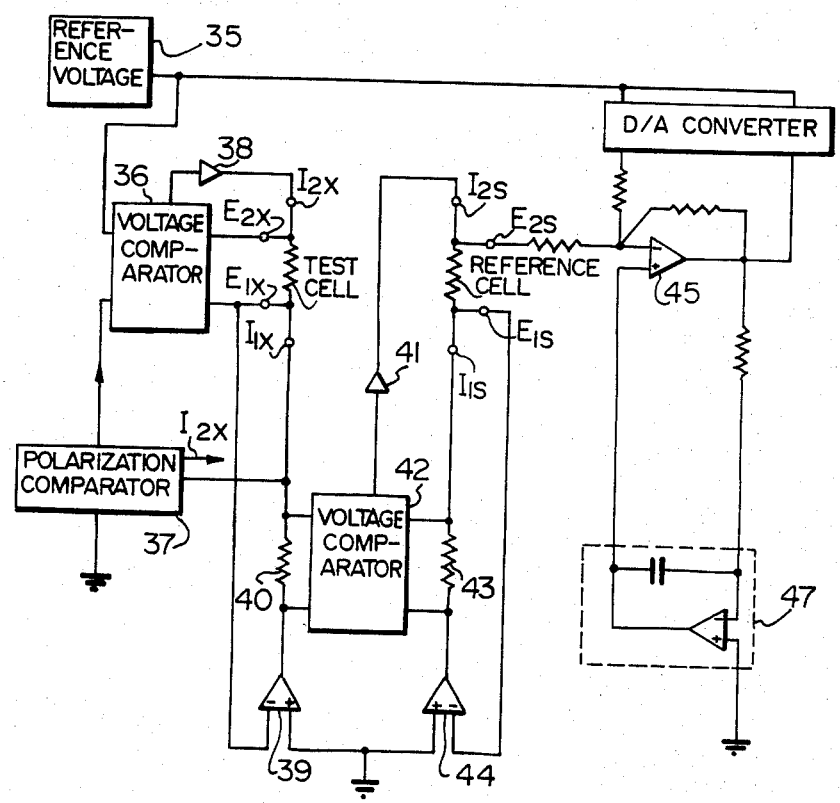
FIG. 3 is an embodiment of the salinometer circuitry.

One embodiment of a measuring circuit in accordance with the present invention is illustrated in block form in FIG. 3. It includes a square wave reference voltage source 35 with voltage $V_{ref}$ which is applied to a voltage comparator 36 together with the output from a polarization compensator 37, which detects and corrects for current unbalance caused by any polarization potentials on the voltage electrodes $E_{1x}$, $E_{2x}$. From current amplifier 38, a current is driven through the cell 17 between the current electrodes $I_{1x}$, $I_{2x}$, so as to maintain a constant square wave voltage across potential electrodes $E_{1x}$ and $E_{2x}$. The drive current is fed through electrode $I_{2x}$ and at the same time a current is drawn from electrode $I_{1x}$ by amplifier 39 through a resistor 40, such that electrode $E_{1x}$ is held at ground potential at all times. This ensures that there is no ac current in the line to the heat exchanger 14. Consequently the squarewave component of the current in electrode $I_{1x}$ is exactly that required to generate the standard squarewave voltage across the potential electrodes $E_{1x}$, $E_{2x}$ and is, therefore, proportional to the conductivity of the sample water in the cell 17.

The standard or reference water cell in FIG. 1 functions in the same way. In this case, however, a drive amplifier 41 drives a current into electrode $I_{2s}$, through the reference cell and out of $I_{1s}$. This current is identical to the current in the sample cell. This is achieved by using a comparator 42 which is coupled across resistor 40 and across a resistor 43 through which the reference current is drawn by amplifier 44, to control the amplifier 41.

The square-wave voltage across the potential leads $E_{1s}$, $E_{2s}$ of the reference cell is proportional to the ratio of the conductances of the sample x and standard s cells 4 and 7. That is, if $k_x$ and $k_s$ are the cell constants of the unknown and standard cells 4 and 7, and $C_x$ and $C_s$ are the water conductivities, then $$I_x = V_x k_x C_x = V_s k_s C_s$$

therefore, $$V_s = V_x k' \frac{C_x}{C_s} = V_x k' R_t \quad (2)$$

$$R_t = \frac{V_s}{V_x} k'$$

where $k' = k_x/k_s$ is the ratio of the cell constants.

In order to accurately measure the potential across the reference cell 7, a null-detector is used. It includes a summing amplifier 45 to which is applied the voltage between electrodes $E_{1s}$ and $E_{2s}$ from across the reference cell 7. A further equal and opposite voltage is applied to the amplifier 45 which is obtained from a D/A converter 46 which is controlled by the amplifier 45 and which also uses the reference squarewave voltage as its reference source. A polarization compensation circuit which includes an integrating circuit 47 is coupled to the output of amplifier 45 which integrates any dc and controls the bias of amplifier 45.

With due allowance for the respective cell constants and for the deviation from exactly S=35 (a conductivity ratio of 1) of the standard seawater, a display reading the output setting of the D/A converter 46 may then be used to calculate conductivity ratio $R_t$ of the sample water using equation 2. Then with a knowledge of the approximate temperature of the bath, the salinity of the sample water may be determined from equation 1. The temperature may be determined using the present measuring circuit without additional thermistor circuits or the like by using the conductivity of the standard seawater itself as the measure of temperature. This is done by substituting a fixed resistor for the sample cell 4 chosen to give an appropriate range of readings on the display for temperatures between 15° and 35° C. A simple graph or table allows one to read off the temperature to sufficient accuracy. Also, the fact that the ratio is trimmed to give correct S values with the particular standard seawater being used ensures that a universal calibration curve calculated from the new equation for the effect of temperature on the conductivity of standard seawater, $$r_t = \sum_{i=0}^{4} c_i t^i \quad (3)$$

where $r_t$ is the correction to $R_t$ at temperature t; and
$c_i$ are the coefficients for the polynomial;

can be used at all times.

Many modifications in the above described embodiments of the invention can be carried out without departing from the scope thereof, and, therefore, the scope of the present invention is intended to be limited only by the appended claims.

We claim:

1. A salinometer comprising:
   a reference water channel and a sample water channel, each of the channels including means for feeding predetermined water into the channel;
   reference conductivity cell means in the reference water channel and sample conductivity cell means in the sample water channel each conductivity cell means having a water inlet and a water outlet, and each conductivity cell means having first, second, third and fourth electrodes immersed sequentially in the water in the direction of flow, the first and third electrodes being potential electrodes and the second and fourth electrodes being current electrodes;
   means for maintaining the temperature of the water in the two cell means substantially the same;
   first circuit means for controlling the current through each of the second electrodes such that the voltages at the first electrodes are maintained at a potential substantially identical to the voltage in the temperature maintaining means, thereby preventing electrical leakage from the water inlet of each cell;
   second circuit means for driving a current through the fourth electrode of the sample water conductivity cell means thereby generating an ac voltage $V_x$ between the first and third electrodes of the sample water conductivity cell means; and
   third circuit means for controlling the current through the fourth electrode of the standard water conductivity cell means such that the current in the second electrode of the standard water conductivity cell means has a fixed ratio to the current in the second electrode of the sample water conductivity cell means, whereby the conductivity ratio $R_t$ between the reference water and the sample water is determined as a function of the voltage $V_s$ between the reference cell means first and third electrodes and the voltage $V_x$ between the sample cell means first and third electrodes.

2. A salinometer as claimed in claim 1 wherein the temperature maintaining means includes a common liquid bath and a heat exchanger for each channel connected to the cell means, the heat exchanger being located in the liquid bath.

3. A salinometer as claimed in claim 2 wherein the heat exchanger includes a metal tubing, and the tubing in the reference channel is fixed to the tubing in the sample channel.

4. A salinometer as claimed in claim 1 wherein the second circuit means provides a current whereby the voltage $V_x$ between the first and third electrodes of the sample water conductivity cell means is a square wave.

5. A salinometer as claimed in claim 4 wherein the voltage $V_x$ is substantially constant.

6. A salinometer as claimed in claim 5 wherein the second circuit means further includes means for compensating for a polarization potential between the first and third electrodes of the sample water conductivity cell means.

7. A salinometer as claimed in claim 6 wherein the third circuit means includes null detector means for measuring the potential $V_s$ between the first and third electrodes of the reference water conductivity cell means.

8. A salinometer as claimed in claim 6 wherein the third circuit means further includes means for compensating for a polarization potential between the first and third electrodes of the reference water conductivity cell means.

* * * * *